United States Patent [19]
Yager et al.

[11] Patent Number: 5,597,255
[45] Date of Patent: Jan. 28, 1997

[54] LIQUID CONTAINER WITH APPLICATOR

[76] Inventors: Timothy J. Yager; David C. Yager, both of 1836 Laburumn Ave., Chico, Calif. 95926

[21] Appl. No.: 476,600

[22] Filed: Jun. 6, 1995

[51] Int. Cl.⁶ ............................... A47L 1/15; A47L 13/17
[52] U.S. Cl. ........................................ 401/207; 401/205
[58] Field of Search ................................ 401/205, 207, 401/202, 290

[56] References Cited

U.S. PATENT DOCUMENTS

| | | | |
|---|---|---|---|
| 673,918 | 5/1901 | Murray | 401/207 X |
| 2,567,764 | 9/1951 | Davies | 15/114 |
| 2,742,660 | 4/1956 | Van Esley | 15/138 |
| 2,896,236 | 7/1959 | Bartkewitz | 401/202 |
| 4,008,968 | 2/1977 | Hobbs | 401/207 |
| 4,127,911 | 12/1978 | Cup | 15/210 |
| 4,580,588 | 4/1986 | Swope, Jr. | 401/290 X |
| 4,762,433 | 8/1988 | Bergeson et al. | 401/206 |
| 4,925,327 | 5/1990 | Wirt | 401/205 |
| 4,961,662 | 10/1990 | Chow et al. | 401/207 X |
| 4,998,838 | 3/1991 | Cancelosa et al. | 401/207 X |
| 5,165,811 | 11/1992 | MacLeod | 401/23 |
| 5,240,339 | 8/1993 | DeForest et al. | 401/207 |
| 5,299,877 | 4/1994 | Birden | 401/207 X |
| 5,353,819 | 10/1994 | Kahn et al. | 401/207 X |

*Primary Examiner*—Steven A. Bratlie
*Attorney, Agent, or Firm*—Bernhard Kreten

[57] ABSTRACT

A device (10) for a liquid application includes a liquid container (11), a hollow tubular liquid conduit (15) for liquid to pass to an applicator (16) secured to an applicator support (19). The applicator (16) includes a plate (20) with a hole (21) and a porous foam material (23) glued to the plate (20) above the hole (21). The applicator (16) is secured to the applicator support (19) by a ledge (39) with the holding lip (41) at three sides of the applicator support (19) and by a latching rib (42) on the fourth side. A set of the applicators (16) with different sizes of the holes (21) is provided to replace applicator (16) in use, if a different flow rate is desired or if the original applicator becomes unusable.

20 Claims, 4 Drawing Sheets

LIQUID CONTAINER WITH APPLICATOR

FIELD OF THE INVENTION

The present invention relates to a liquid applicator for use on a container to apply the liquid content of the container to a surface of different objects, and more particularly, to new and useful improvements in such applicators providing a needed flow of liquid and a desired degree of wetting to the surface.

BACKGROUND OF THE INVENTION

Liquid containers with applicators to apply liquid contained therein to different surfaces are known in the art. These applicators include a sponge wetted by the liquid poured out from the container and may be used for various purposes, as for example, washing devices, painting or polishing devices, body lotion applicators, etc.

For instance, U.S. Pat. No. 2,742,660 describes a polish applicator, including a hollow handle having a downwardly-projecting head at its front end with a discharge opening in its bottom surface and an absorbent pad having a backing plate secured thereto. Resilient clips are detachably secured to the head to support the pad under the bottom of the head and over the opening in the head. The backing plate has an opening aligned with the discharge opening of the head, which has a passage leading from the handle to the discharge opening.

A device of U.S. Pat. No. 4,008,968, used for washing dishes and the like, comprises a hollow handle that may be filled with detergent, and a removable sponge. The small aperture in the bottom of the handle permits the detergent to seep into the sponge which may be eternally wetted for use. In one embodiment, the sponge is permanently secured to a mounting plate having an aperture therethrough. The handle has a small nozzle which interlocks with the hole in the mounting plate, and the handle further comprises a flange or clip for receiving an edge of the mounting plate. In an alternate embodiment, the handle may terminate in a straight flat edge and the mounting plate may be provided with a flange or slip for accommodating the edge of the handle. In still another preferred embodiment, the handle is provided with two spaced nozzles or spouts, one of which has a passage and the other of which is closed. These spouts alone secure the sponge mounting plate to the device.

A body lotion applicator of U.S. Pat. No. 5,240,339 is intended for application of a body lotion to parts of the body that are originally beyond reach. The device has an extended applicator head for reaching the back and other portions of the body that are difficult to reach. An elongated arm serves as a handle and a conduit for conducting body lotion from a conventional bottle to the applicator head, which includes a face plate and a porous sponge affixed thereto by a retaining ring.

U.S. Pat. No. 4,762,433 discloses a fluid applicator for shoes and the like having a foam head and includes a valve means which seals automatically when not in use in order to eliminate clogging of its discharge aperture and to keep its fluid passage-way and associated valve means unclogged as well.

Although having certain improvements useful in their particular applications, the above-mentioned applicators do not have a means for regulating a flow of liquid from a liquid container to a sponge. In some areas, as for example, antiseptic surgery preparation and others, it is important to prevent dripping of the solution onto the skin. The liquid applicator of U.S. Pat. No. 4,925,327, which is concerned with this problem, includes a porous metering insert to control delivery of the antiseptic solution to the sponge. The metering insert and the sponge are held together by a variety of suitable means, including adhesive bonding, and are disposed over a major orifice through which the liquid flows.

The present invention provides another solution for regulating the flow of liquid from a liquid container to an applicator.

SUMMARY OF THE INVENTION

It is, therefore, an object of the present invention to provide an improved liquid container with an applicator having a liquid flow regulating feature.

It is another object of the present invention to provide a liquid container with a set of replaceable applicators, each allowing a certain rate of liquid flow. It is still another object of the present invention to provide a liquid container having a simple yet reliable means for holding an applicator in place and permitting easy replacement.

According to the present invention, an article for a liquid application includes a liquid container, an applicator support, an applicator removably secured to the applicator support, and a hollow tubular liquid conduit conducting liquid from the liquid container to the applicator.

The applicator has a rectangular plate, a tab integrally connected to the rectangular plate, and a recess between the plate and the tab.

A hole is located substantially in the center of the plate, and a porous foam material is secured on the plate above the hole.

The application support includes a substantially rectangular bottom having a central aperture, a ledge extended at right angle from the bottom at its three sides, and a latching rib on the fourth side of the bottom. The ledge has a holding lip at the upper edge of the ledge.

When the applicator is slid into the applicator support, the lip holds the rectangular plate of the applicator at the three edges of the rectangular plate, and the latching rib on the applicator support engages the recess on the applicator, thereby holding the applicator in place. The hole on the applicator is substantially co-axial with the central aperture on the bottom at the applicator support.

A plurality of applicators with holes of distinctive size can be used in the article of the present invention for different flow rates desired.

Each applicator can be slid out and replaced with a new applicator if a different flow rate is desired or if the applicator becomes clogged or otherwise unusable.

The porous foam material is of substantially rectangular shape and does not cover the edges of the plate of the applicator to be secured under the lip. The article includes a knurled threaded cap removably securing the liquid conduit to the liquid container.

In another aspect, the present invention may be also viewed as a device for applying a liquid to a work surface, wherein the device has a reservoir connected to an opening by a conduit. The improvement to the device comprises a plurality of applicators. Each applicator comprises a substantially rectangular plate having a hole formed therein, a foam applicator carried by the plate and communicating with the hole, are a tab on the end of the plate. The device has a slotted channel formed therein above the opening for slidably receiving a selected one of the plates with a "snap" fit therebetween, such that the hole in the plate registers with the opening in the device, and such that the tab on the end of the plate is externally accessible of the device, thereby facilitating a convenient removal of the plate and replacement thereof.

These and other objects of the present invention will become apparent from a reading of the following specification taken in conjunction with the enclosed drawings.

DESCRIPTION OF PREFERRED EMBODIMENTS

Figure 1:
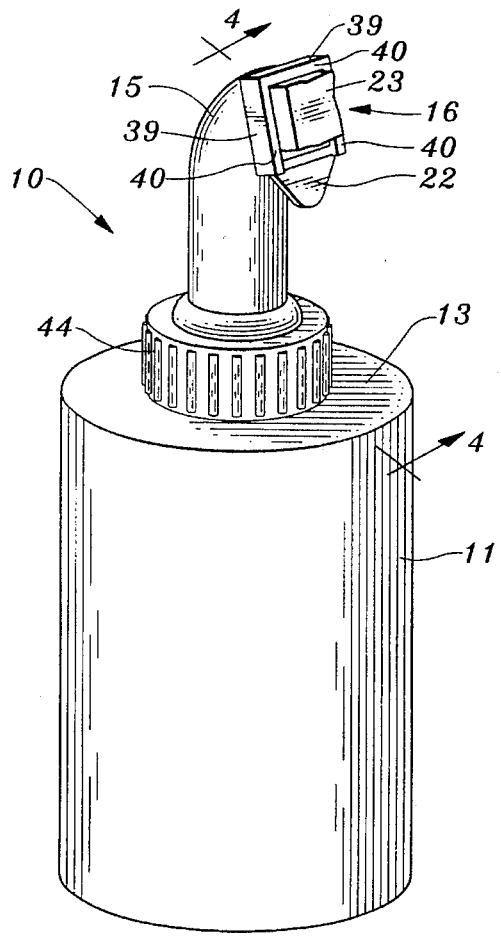
FIG. 1 is a perspective view of the device of the present invention.
Figure 2:
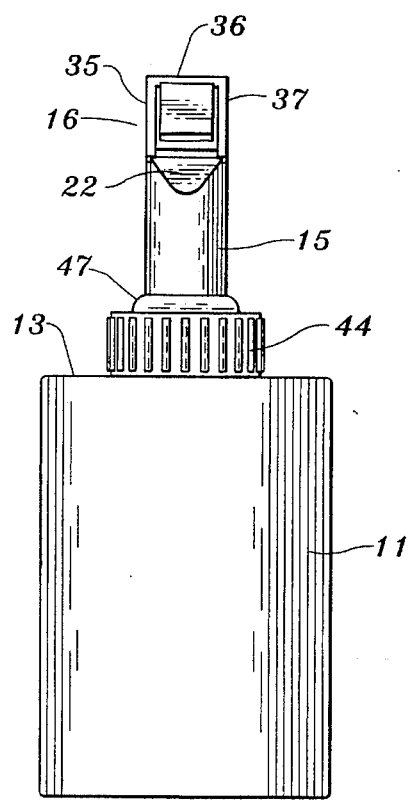
FIG. 2 is a front view thereof.
Figure 4:
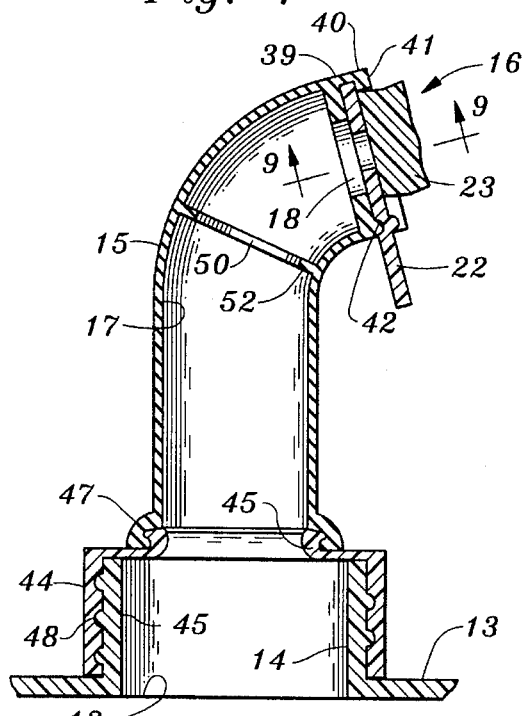
FIG. 4 is a cross-sectional view of FIG. 1 taken along lines 4—4 of FIG. 1.
Figure 3:
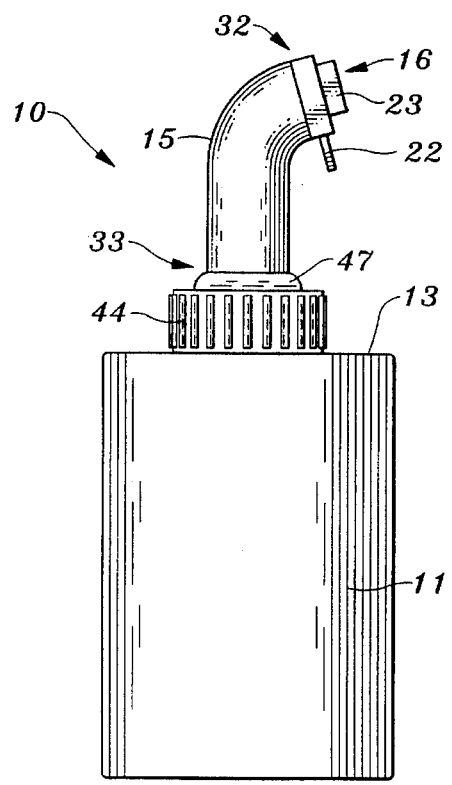
FIG. 3 is side view thereof.
Figure 5:
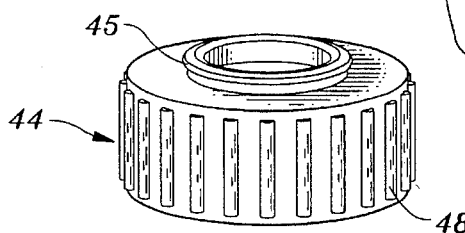
FIG. 5 is an exploded perspective view of the device of the present invention.

With reference to FIGS. 1–11, a device 10 for a liquid application includes a liquid container 11 for holding a liquid (not shown). The liquid may be a detergent, antiseptic solution, paint, glue, etc. for each particular application. Referring now to FIG. 1 and 4 the liquid container 11 has an orifice 12 on the upper portion 13 of the liquid container 11. Externally-threaded sleeve 14 on the upper portion 13 of the liquid container 11 surrounds the orifice 12 and extends above the upper portion 13 by a certain height. The liquid container 11 (as shown) has a cylindrical shape; however, it can be of any convenient shape to keep a liquid. A hollow tubular liquid conduit 15 is removably secured to the sleeve 14 on the liquid container 11 to transfer the liquid from the liquid container 11 to applicator 16. Referring now to FIGS. 3, 4 and 5, walls 17 of the liquid conduit 15 form a conduit for the liquid which flows out from the liquid container 11 through the orifice 12, passes through the liquid conduit 15, and comes up to the applicator 16 through a central aperture 18 in an applicator support 19.

Figure 7:
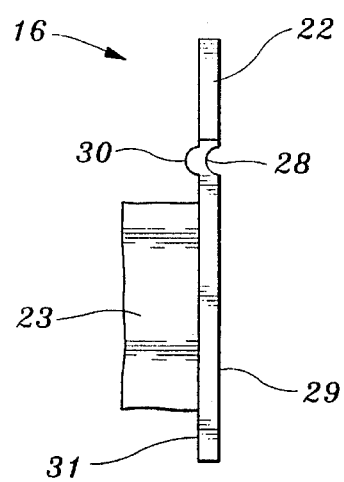
FIG. 7 is a side view of the applicator of the present invention.
Figure 8:
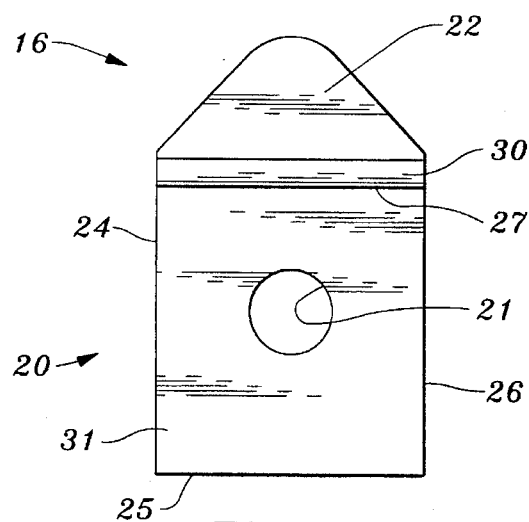
FIG. 8 is a front view of the plate of the applicator of the present invention.

As seen in FIGS. 7 and 8, the applicator 16 includes a substantially rectangular plate 20 with a hole 21 substantially in the center of the plate 20 and a tab 22. A porous foam material 23 is of substantially rectangular shape and adapted to be attached to the outer face of plate 20. The material 23 does not cover the whole surface of the plate 20, leaving edges 24, 25, 26, 27 free for engagement with the applicator support 19 (as will be explained below). As seen in FIGS. 5 and 7, the material forming a recess 28 connects the plate 20 and the tab 22 on a bottom 29 of the applicator 16 on the inner side opposite foam material 23. The recess 28 forms a bump 30 on an outer surface 31 of plate 20.

The applicator support 19 for supporting and removably holding the applicator 16 is positioned on the end 32 of the liquid conduit 15 opposite to the end 33 by which the liquid conduit 15 is attached to liquid container 11.

Figure 4A:
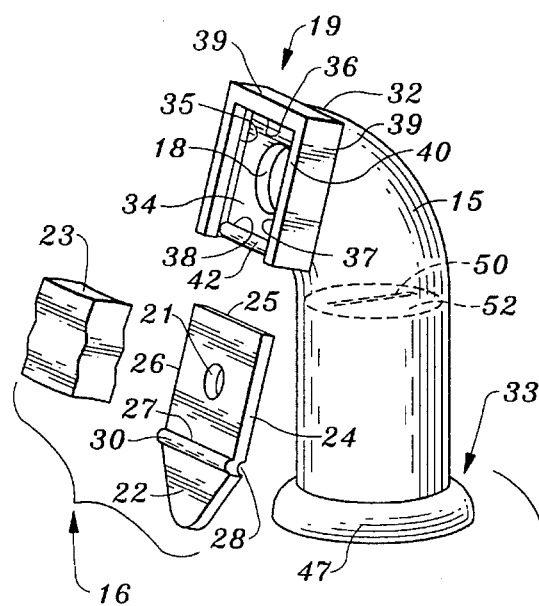
FIG. 4A is an alternative to FIG. 4.
Figure 4A:
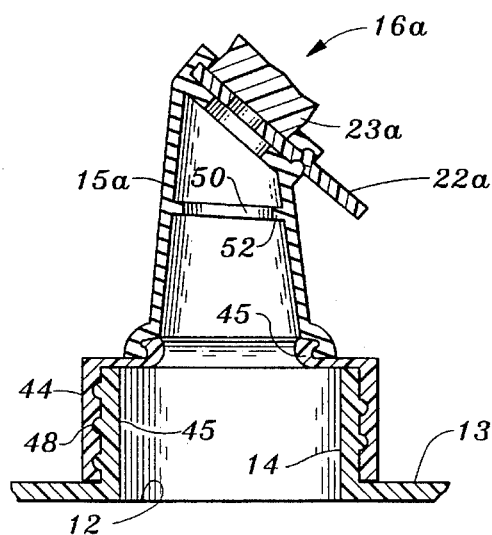
Figure 5A:
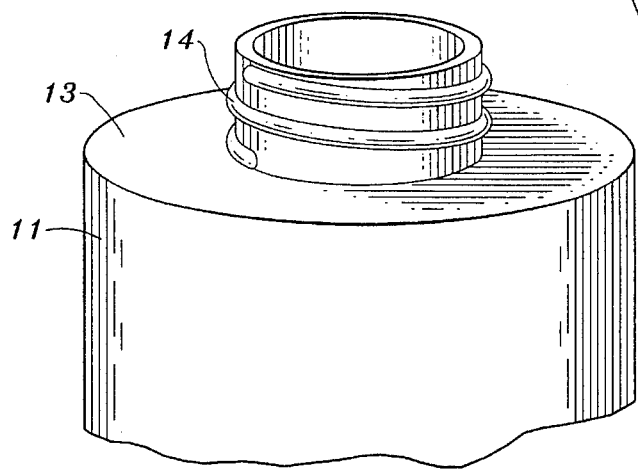
FIG. 5A is an alternative to FIG. 5.
Figure 5A:
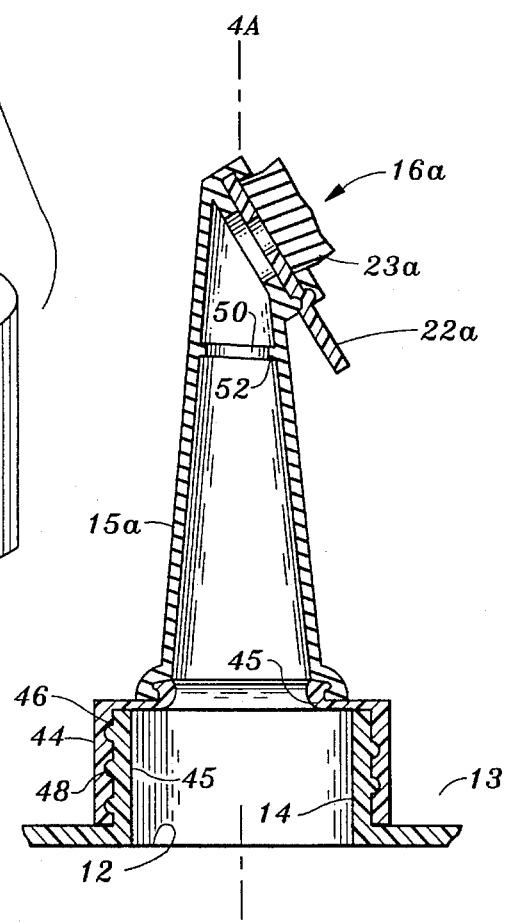
Figure 6:
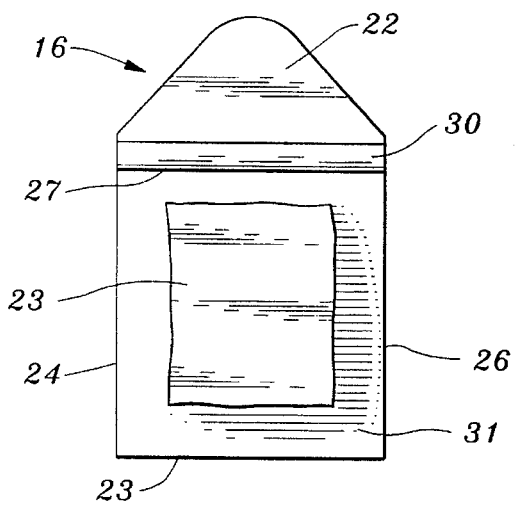
FIG. 6 is a front view of the applicator of the present invention.

FIGS. 4 and 5 suggest that the conduit 15 is of constant circular cross-section with an arcuate top portion, adjacent the applicator 16. FIGS. 4A and 5A show an alternative where conduit 15A is a substantially non-curved truncated cone. Note the applicator 16 has a high point substantially coincident with the long axis L.A. of the device for stable use without inducing a turning moment. The applicator support 19 in FIG. 5 and 9 includes a substantially rectangular bottom 34 having four sides 35, 36, 37 and 38 and the central aperture 18. A ledge 39 commences running from the bottom 34 at its three sides 35, 36 and 37 at a right angle to the bottom 34. On the upper edge 40 of the ledge 39, a holding lip 41 (FIG. 9) is positioned to hold the edges 24, 25, 26 of the plate 20. A latching rib 42 (FIG. 5) is extended along the side 38 of the bottom 34.

When the applicator 16 is slid into the applicator support 19, the edges 24, 25, 26 of the plate 20 are held under the holding lip 41; and the recess 28 of the bottom surface of the applicator 16 is snapped over the latching rib 42, thereby securing the applicator to the applicator support, while the central aperture 18 is co-axial to the hole 21 on the applicator 16. The liquid flows through the central aperture 18 and through the hole 21 and wets the porous foam material 23.

When the applicator 16 should be replaced, the user lifts out the tab 22, thereby separating the recess 28 and the latching rib 42 (FIG. 10), and then pulls the tab 22 out, thereby sliding the applicator 16 out from the applicator support 19. A new applicator 16 can then be slid in by driving the applicator hole 21 into co-axial alignment with central aperture 18 and recess 28 into engagement with latching rib 42.

Figure 8A:
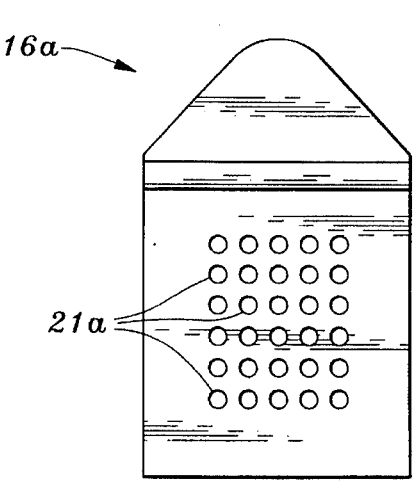
FIG. 8A is an alternative to FIG. 8.
Figure 9:
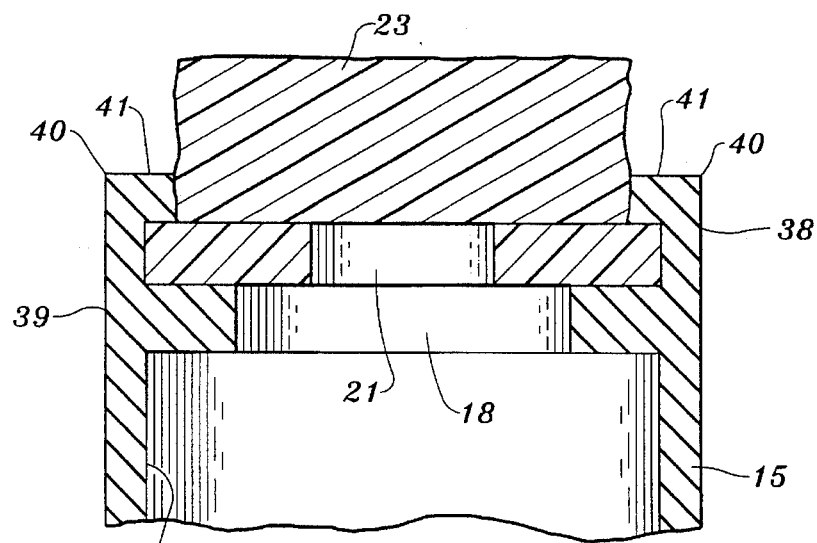
FIG. 9 is a cross-sectional view of FIG. 4, taken along lines 9—9 of FIG. 4 and drawn to an enlarged scale.
Figure 10:
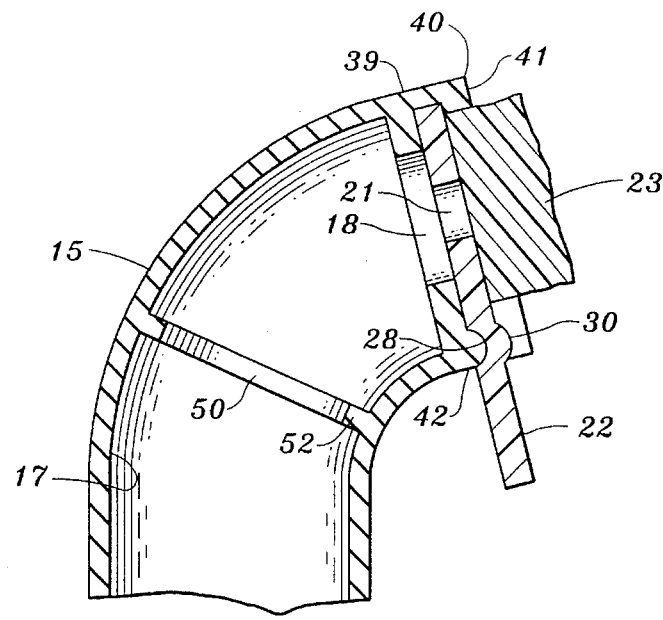
FIG. 10 is an enlarged partial view of FIG. 4.
Figure 11:
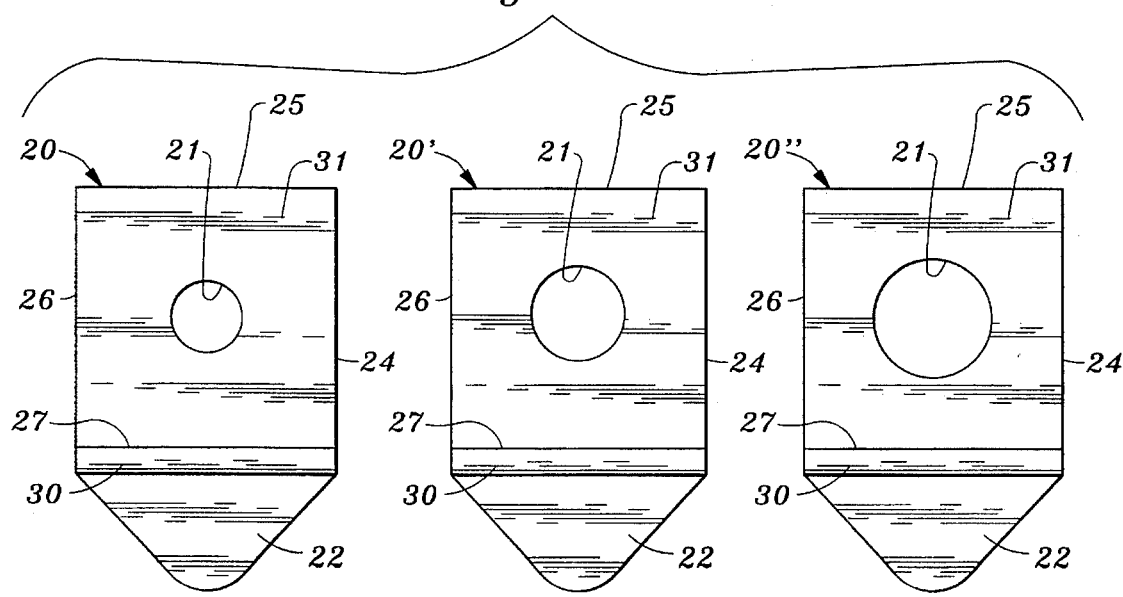
FIG. 11 is a view showing a set of applicators, each having a hole of distinctive size.

As shown in FIG. 11, a set of rectangular plates (20, 20', 20") is displayed ready to be attached to the device 10. The set includes plates 20 of a similar design, but each having the hole 21 of a distinctive size. This allows different applications, different liquids, different rates of liquid flow, and also different degrees of wetting the porous foam material 23. To provide a lower rate of flow, the plate 20 with a smaller hole 21 is used. When the rate of flow is desired to be higher, the plate 20 is replaced by another plate (20' or 20") with a bigger hole 21. A matrix of holes 21a are shown in FIG. 8A and allow direct contact of the liquid to the foam 23, rather than relying on wicking. As shown, the holes 21a are oriented into rows and columns. Various densities of foam can also be used to control the rate at which the liquid is dispensed.

Another device to control flow rate of the liquid reaching the applicator 16 is shown in FIGS. 4 and 5. An internal disc 52 with a central slit opening 50 is formed from the same material that composes the walls 17 of liquid conduit 15. One other purpose of the internal disc 52, besides controlling flow rate of the liquid leaving container 11 and going to applicator 16, is to restrict or prevent the entry of air into container 11.

The device 10 also includes a knurled 48 threaded cap 44 for removable connection of the liquid conduit 15 and the liquid container 11. The knurled threaded cap 44 has an upper externally threaded sleeve 45, and its internal side walls 46 are threaded to engage with the threads on the externally-threaded sleeve 14 surrounding the orifice 12 on the upper portion 13 the liquid container 11.

As seen in FIGS. 4 and 5, the hollow tubular liquid conduit 15 has an internally threaded flange 47 on the end 33. The threads inside the flange 47 engage with the threads of the upper sleeve 45. Therefore, the knurled threaded cap 44 provides a sealed connection between the liquid container 11 and the liquid conduit 15.

External side walls 48 of the knurled 48 threaded cap 44 are grooved or knurled in order to attain convenience in use and distinctive design. Also, the parts of the device 10 can be made of different colors or be transparent.

Many modifications may be made without departing from the basic spirit of the present invention. Accordingly, it will be appreciated by those skilled in the art that within the scope of the appended claims the invention may be practiced other than has been specifically described herein.

We claim:

1. In an article for a liquid application, including:

a liquid container having an orifice on an upper portion thereon, a hollow tubular liquid conduit having a first and a second end, respectively, said liquid conduit being connected by the second end to the orifice in the liquid container, an applicator support on the first end of the liquid conduit, and an applicator removably secured to the applicator support, the applicator including a porous foam material, wherein the improvement comprises;

in the applicator support a substantially rectangular bottom, said bottom having a first, a second, a third and a fourth side, a ledge extending at substantially right angles from said first, second and third sides of the bottom, said ledge having an upper edge, a holding lip being provided at the upper edge on the ledge, and a latching rib on the fourth side of the bottom, such that when the applicator is slid into the applicator support, said holding lip and the latching rib engage the applicator, thereby removably securing the applicator to the applicator support, the applicator including a recess which receives said latching rib to secure the applicator to said applicator support.

2. The article of claim 1, wherein said bottom of the applicator support has a central aperture.

3. The article of claim 1, wherein said applicator includes a substantially rectangular plate, a tab integrally connected to the plate, the plate and the tab having said recess therebetween, a hole substantially in the center of the plate, and the porous foam material being on the plate above the hole.

4. The apparatus of claim 3, further including a plurality of applicators, each having a hole of a distinctive size.

5. In an article for a liquid application, including:

a liquid container having an orifice on an upper portion thereon, a hollow tubular liquid conduit having a first and second end, respectively, said liquid conduit being connected by the second end to the orifice on the liquid container, an applicator support on the first end of the liquid conduit, the applicator support having a securing means, an applicator removably secured to the applicator support, the applicator having a porous foam material, wherein the improvement comprises:

the applicator comprising a substantially rectangular plate, the rectangular plate having respective sides, a tab, integrally connected to the plate, a hole substantially in the center of the plate to provide a first control of liquid therebeyond, the porous foam material secured on the plate above the hole, such that the applicator being removably secured to the applicator support by the securing means engaging the respective sides on the plate, and a disc located in said liquid conduit transverse to a liquid flow path and having a slit passing therethrough to provide a second control of liquid therebeyond.

6. The article of claim 5, further including a plurality of applicators, each having a hole of the distinctive size.

7. The article of claim 5, wherein the applicator includes a recess located between the plate and the tab and opposite said porous foam material and the applicator support includes a substantially rectangular bottom, said bottom having a first, a second, a third and a fourth side, and the securing means including: a ledge extending at substantially right angle from said first, second and third sides of the bottom, said ledge having an upper edge, a holding lip being provided at the upper edge of the ledge, and a latching rib on the fourth side of the bottom, such that when the applicator is slid into the applicator support, the applicator is removably secured to the applicator support by said holding lip and by said latching rib engaging said recess.

8. The article of claim 7, wherein said bottom of the applicator support has a central aperture, substantial co-axial with the hole in the plate of the applicator.

9. The article of claim 5, further including a knurled threaded cap, the knurled threaded cap having an upper sleeve, wherein the liquid container includes an orifice on an upper portion thereon and a threaded sleeve surrounding said orifice, wherein the hollow tubular liquid conduit has an internally-threaded flange surrounding an end of the liquid conduit opposing the applicator support, wherein the knurled threaded cap is positioned over the threaded sleeve on the liquid container, and wherein the internally-threaded flange on the liquid conduit is positioned over the upper sleeve on the knurled threaded cap, thereby removably securing the liquid conduit to the liquid container.

10. The article of claim 5 wherein said conduit is in the shape of a straight walled truncated cone.

11. The article of claim 10 wherein the top of said applicator support is at the apex of said truncated cone.

12. The article of claim 11 wherein the outer surface of said porous foam material is at an angle of at least 45° to the plane of said orifice of said liquid container.

13. The article of claim 5, wherein the porous foam material is of substantially rectangular shape and does not cover the edges of the plate of the applicator, secured under the lip.

14. In a device for applying a liquid to a work surface, with the device having a reservoir connected to an opening by a conduit, wherein the improvement comprises:

a plurality of removeable applicators, each applicator comprising a substantially rectangular plate having a hole formed therein;

a foam applicator carried by said plate and communicating with the hole;

a tab at one edge of said plate; and the conduit at an end opposite said reservoir having a slotted channel defined by a three sided retention means formed therein over the opening and adapted to slideably receive a selected one of said plates providing a snap engagement therebetween formed by a recess on said plate and a latching rib located on a fourth open side of said three sided retention means, such that the hole in said plate registers with the opening in the device, and such that the tab on the end of said plate is accessible to grasping, thereby facilitating a convenient removal of said plate and replacement thereof by pulling said plate recess over said latching rib and away from said three sided retention means.

15. The device of claim 14 further including a slotted internal disc located within said conduit to both meter flow and minimize oxidation of the liquid with the reservoir by limiting air access when said device is not in use.

16. The device of claim 15 wherein said conduit is configured as a truncated cone.

17. The device of claim 16 wherein said applicator is located at a top of said cone.

18. The device of claim 17 wherein said foam applicator obscures the hole and extends beyond an outer periphery of the hole.

19. The device of claim 18 wherein foam controls the rate at which the liquid is distributed by its porosity and density, said foam is located on said plate, overlying the hole.

20. A liquid dispenser comprising in combination:

an open topped container having an externally threaded opening, a conduit having a first end which receives an applicator thereat and a second end including an internal thread complemental to said threaded opening for attachment thereto, a restrictive disc located in said conduit blocking said conduit and having a slit passing therethrough to meter liquid flow therebeyond and to minimize oxidation, a hole at said conduit first end further metering liquid therebeyond, an applicator receiving head surrounding said hole and including a three sided frame including a support lip which receives an applicator plate having three sides complemental to said frame to be received slideably therewithin, a fourth side of said frame having a latching rib, said applicator plate having a recess complemental to said latching rib on a fourth side thereof, said recess oriented to overlie said latching rib, a hole in said applicator plate in communication with said conduit first end hole, a pull tab on a side of said recess opposite from said plate hole to facilitate plate removal, and a dispensing foam on said plate facing upwardly away from said conduit first hole and overlying said plate hole to dispense liquid therefrom.

* * * * *